(12) United States Patent
Just et al.

(10) Patent No.: US 9,119,548 B2
(45) Date of Patent: Sep. 1, 2015

(54) DEVICE AND METHOD FOR SECONDARY DENTAL CARIES DIAGNOSIS

(75) Inventors: Marcin Just, Wroclaw (PL);
Przemyslaw Los, Zurawice (PL);
Michal Tyc, Wroclaw (PL)

(73) Assignee: Numed SP Z O.O., Warsaw (PL)

( * ) Notice: Subject to any disclaimer, the term of this patent is extended or adjusted under 35 U.S.C. 154(b) by 0 days.

(21) Appl. No.: 14/112,649

(22) PCT Filed: Apr. 13, 2012

(86) PCT No.: PCT/PL2012/050008
§ 371 (c)(1),
(2), (4) Date: Jan. 3, 2014

(87) PCT Pub. No.: WO2012/144913
PCT Pub. Date: Oct. 26, 2012

(65) Prior Publication Data
US 2014/0106293 A1 Apr. 17, 2014

(30) Foreign Application Priority Data

Apr. 21, 2011 (PL) .................................... PL394638

(51) Int. Cl.
*A61B 5/053* (2006.01)
*A61B 5/00* (2006.01)
(Continued)

(52) U.S. Cl.
CPC ............... *A61B 5/0534* (2013.01); *A61B 5/053* (2013.01); *A61B 5/4547* (2013.01); *A61C 19/04* (2013.01); *G01N 33/48707* (2013.01); *A61B 5/682* (2013.01)

(58) Field of Classification Search
CPC ...... A61C 19/04; A61B 5/053; A61B 5/0534; A61B 5/4547; A61B 5/682
USPC .................................................... 433/32, 27
See application file for complete search history.

(56) References Cited

U.S. PATENT DOCUMENTS 4,537,573 A * 8/1985 Sunada ........................... 433/32
5,306,144 A 4/1994 Hibst et al.
(Continued)

FOREIGN PATENT DOCUMENTS

EP 0862896 A3 4/2001
JP 5337142 12/1993
(Continued)

OTHER PUBLICATIONS

International Searching Authority, International Search Report issued in corresponding International Application No. PCT/PL2012/050008 filed Apr. 13, 2012, 11 pages.
(Continued)

*Primary Examiner* — Ralph Lewis
(74) *Attorney, Agent, or Firm* — Wood, Herron & Evans, LLP

(57) ABSTRACT

A secondary caries detection device includes a current generating device configured to generate a current having the form of a sinusoidally varying signal with a frequency chosen from the range of frequencies from 200 Hz to 100 kHz and a chosen amplitude from the range of 50 mV to 5 V. The secondary caries detection device also includes a plurality of preamplifiers of high sensitivity and linearity with phase-sensitive measuring components sensitive to the chosen frequency and integral multiples of the chosen frequency. The secondary caries detection device further includes a microprocessor control unit connected to the current generating device and the plurality of preamplifiers. In addition, the secondary caries detection device includes at least one fixed electrode configured for placement on a mucous membrane of an oral cavity and at least one moveable electrode configured for placement on a surface of a tooth, both of which are connected to the current generating device and the plurality of preamplifiers.

9 Claims, 5 Drawing Sheets

(51) Int. Cl.
 *A61C 19/04* (2006.01)
 *G01N 33/487* (2006.01)

(56) References Cited

U.S. PATENT DOCUMENTS

| | | | | |
|---|---|---|---|---|
| 6,230,050 | B1* | 5/2001 | Pitts et al. | 600/547 |
| 6,845,265 | B2* | 1/2005 | Thacker | 600/547 |
| 2006/0167372 | A1* | 7/2006 | Kusano | 600/547 |
| 2008/0032255 | A1* | 2/2008 | Pitts et al. | 433/32 |
| 2008/0097712 | A1 | 4/2008 | Bruce et al. | |
| 2011/0111361 | A1* | 5/2011 | Kleinberg et al. | 433/32 |

FOREIGN PATENT DOCUMENTS

| | | |
|---|---|---|
| JP | 8233758 | 9/1996 |
| PL | 169583 B1 | 1/1993 |
| WO | 9204630 A1 | 3/1992 |
| WO | 97/42909 A1 | 11/1997 |

OTHER PUBLICATIONS

"The International Caries Detection and Assessment System (ICDAS): an integrated system for measuring dental caries" A. I. Ismail et al., Community Dentistry and Oral Epidemiology, vol. 35, No. 3, Jun. 1, 2007.

Polish Search Report, 1 page, received Sep. 19, 2014.

"How Electrical Caries Detection and Monitoring With CarieScan Can Help Deliver Modern Caries Management" Nigel B. Pitts, Oral Health, Jul. 1, 2010.

* cited by examiner

DEVICE AND METHOD FOR SECONDARY DENTAL CARIES DIAGNOSIS

TECHNICAL FIELD

The invention pertains to a device and method for secondary dental caries detection which can be applied in dentistry.

BACKGROUND

A method for studying biological cells with the aid of stimulating them with sinusoidal alternating current and studying the non-linear response of these cells has been described in the patent application WO 92/04630. The above-mentioned cells are located in the studied analytical environment, for example in the form of a suspension or biological tissue.

The method described in the aforementioned patent application is used to study the properties of the solution or the biological tissue as a whole. In the case of in vivo studies, the existence of complex biological tissue systems which differ significantly as far as biophysical and biochemical parameters are concerned creates the main problem. In in vivo studies, the whole organs will be investigated in the majority of cases rather than tissues or groups of identical cells.

Thus, the method described in the aforementioned patent application could not be used to diagnose secondary caries because a tooth is an organ composed of many tissues whose properties differ significantly, including hard tissues which have unique physical and chemical properties decidedly different from the properties of cell solutions or soft tissues which were supposed to be studied by the method described in the prior art invention.

When studying a tooth using a method from the aforementioned patent application, it is impossible to mechanically separate one selected tissue without destruction.

A tooth is composed of mineral components, electrolytes and biological cells, also those located in soft tissues.

Thus, both the bio-impedance study method (including harmonic response study) of a human tooth in vitro or in vivo as a whole as well as the analysis of the results differ fundamentally from those of the isolated biological tissues.

Electrical properties (conductivity and dielectric permittivity) of a tooth or hard tissue in general are fundamentally different than the ones of soft tissue.

There are other sources of non-linearity in the tooth tissue than the ones described in the aforementioned patent application.

At the moment secondary caries diagnosis is carried out using good eye and bitewing X-rays.

When using the above-mentioned method a tooth should be cleaned from the residue and dried. It also exposes the patient to potentially harmful ionizing radiation. The method is time-consuming and does not offer immediate diagnosis.

There are also modern optical methods, e.g. caries detection device Diagnodent which have a limited scope of detection. Amalgam fillings are not transparent and the performance of the device demonstrates low sensitivity and specificity.

The other method which has a wide application in the enamel quality diagnosis are bio-impedance measurements. They are popular in studying the root canal fillings, and lately have been used to study enamel quality among other things.

Bio-impedance measurements of enamel consist in the analysis of its ac impedance spectrum and allow to determine precisely the enamel dielectric and conductivity parameters which change significantly when the disease processes are present.

This method is especially accurate when the structure of a tooth is known. Moreover, the examination is non-invasive, it does not take much time and the cost of producing a measurement apparatus is relatively low. These advantages have already been used in the commercially available devices for bio-impedance enamel analysis (e.g., www.cariescan.com).

The above-mentioned method demonstrates very high sensitivity [correct identification of carious sites] in a physical rather than medical sense but very low resolution [correct identification of sound sites] which signifies that the response can be influenced by a number of biophysical factors and phenomena such as for example water presence, surface cleanliness including microbiological one. It cannot be used to study secondary caries.

Thus, there is still a need for a method and a device for secondary caries diagnosis which is quick, does not expose patients to ionizing radiation, has high resolution allowing to detect water environment presence such as bacterial microflora or changes in sound enamel caused by secondary caries development. This method should also consider specific electrical properties (conductivity and dielectric permittivity) of a tooth and its filling (the fact that amalgam is not transparent).

SUMMARY

The purpose of the present invention is to study all ac current flow associated nonlinear phenomena which are present in a human tooth and to correlate such a harmonic response with the occurrence of secondary caries which consists in the change of enamel and/or dentine composition and structure as a result of carious processes. Unexpectedly the above-mentioned problem has been solved by the presented invention.

The first embodiment of the invention is a device for secondary caries detection characterized in that it contains a current generating device in the secondary caries detection device's casing, advantageously equipped with the high linearity amplifiers, the current having the form of sinusoidally varying signal, advantageously with one frequency chosen from the range of frequencies from 200 Hz to 100 kHz and amplitude from 50 mV to 5 V; a plurality of preamplifiers, advantageously of high sensitivity and linearity with phase-sensitive detectors measuring components, advantageously with one frequency chosen from the range of frequencies from 200 Hz to 100 kHz as well as its multiples, advantageously integral in principle; microprocessor control unit, advantageously with a miniature keyboard and display unit, and at least one fixed electrode placed on mucous membrane of the oral cavity and at least one moveable electrode to be mounted on a tooth.

It is also advantageous that the device according to the invention, additionally contains an additional interface that can cooperate with the external device, advantageously with a computer or other peripheral device.

The second embodiment of the invention is a method for detection of secondary caries with the aid of at least one moveable electrode placed on the surface of an examined tooth, particularly on the amalgam filling, and at least one fixed electrode secured on a mucous membrane of the oral cavity in the vicinity of the examined tooth which typically comprises:

a) supplying electrical stimulation signal in the form of sinusoidally varying current, advantageously with one frequency chosen from the range of frequencies from 200 Hz to 100 kHz and amplitude from 50 mV to 5 V, b) measurement of amplitude and phase components of the system electrical response, advantageously with one frequency chosen from the range of frequencies from 200 Hz to 100 kHz and its integral multiples, advantageously up to 1 MHz, followed by c) analysis of response spectrum for identification of features characteristic of carious changes.

The method according to the invention is also advantageous because typically the characteristic features of the carious lesion spectrum are correlated with the presence of bacteria causing caries which leads to the conclusion that the lesions are present.

The fact that dental caries have microbiological origin is used as the basis for detection and monitoring of secondary caries with the aid of bio-harmonic measurements according to the invention.

The impedance measurements that have been used so far were not selective enough in comparison with the bio-harmonic measurements according to the invention.

The response of the system obtained during the detection of caries using the bio-harmonic method contains also information concerning biological tissue structure and charge transfer or mass transport processes. All these phenomena together with microbiological processes are used to diagnose secondary caries with high sensitivity and specificity.

BRIEF DESCRIPTION OF THE DRAWINGS

The examples of the invention realization are presented in the figures.

DETAILED DESCRIPTION

EXAMPLE 1

A movable electrode was placed on the surface of a tooth with an amalgam filling and a fixed electrode was secured on the mucous membrane of the oral cavity in the vicinity of the examined tooth.

Then an electrical stimulation signal was applied in the form of sinusoidal waveform of a frequency of 100 kHz.

Then the measurement of amplitude and phase components of the system electrical response of a frequency of 100 kHz and its five integral multiples up to 1 MHz was made.

Next the analysis of response spectrum for identification of features characteristic of carious changes was made. The identical procedure was repeated for a sound tooth.

A simulation of alternating current flow through a sound tooth and a tooth with secondary caries under an amalgam filling in a linear response model was performed.

The simulation was performed using finite element method assuming alternating current flow (a frequency of 10 kHz) on a two-dimensional half of the tooth in the gum with one electrode placed on the mucous membrane and the second one touching the occlusal surface of the tooth.

The existence of an amalgam filling and secondary carious lesion was simulated in a tooth.

Figure 3A:
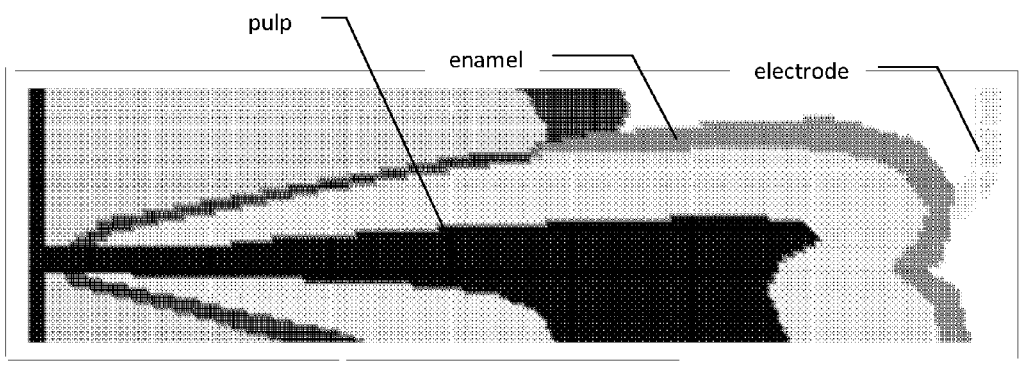
FIG. 3a illustrates exemplary results of the current flow in a sound tooth in relation to the structure in accordance with an embodiment of the invention.
Figure 3B:
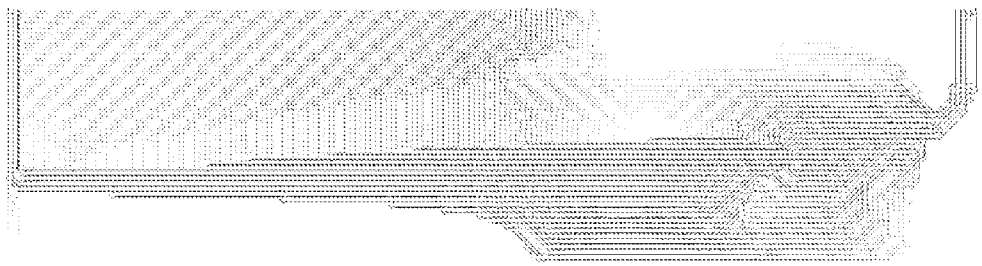
FIG. 3b illustrates exemplary results of the current flow in a sound tooth in relation to the direction of the current flow in accordance with an embodiment of the invention.
Figure 3C:
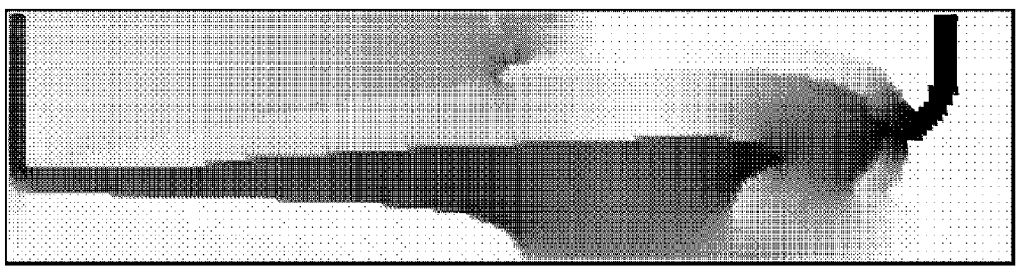
FIG. 3c illustrates exemplary results of the current flow in a sound tooth in relation to the current density distribution in accordance with an embodiment of the invention.
Figure 4A:
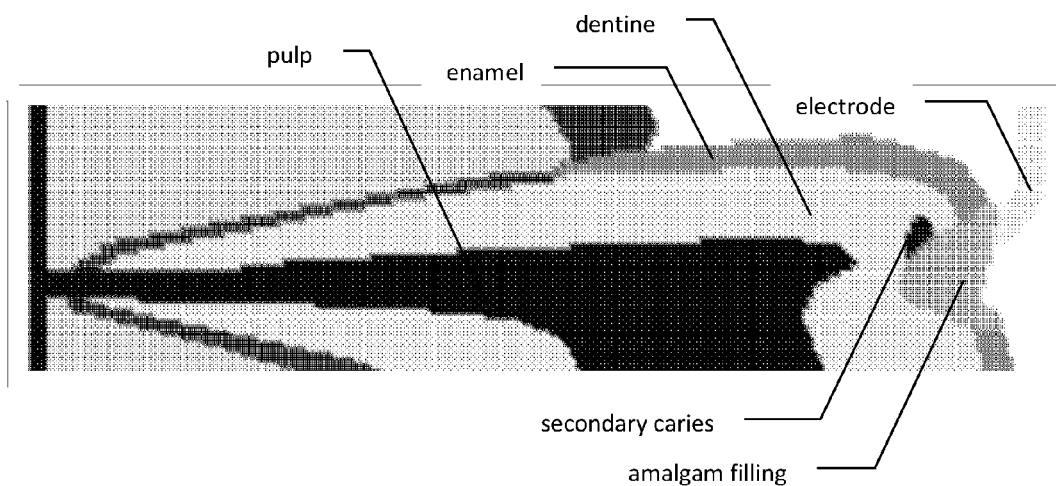
FIG. 4a illustrates exemplary results of the current flow in a tooth with secondary caries under an amalgam filling in relation to the structure in accordance with an embodiment of the invention.
Figure 4B:
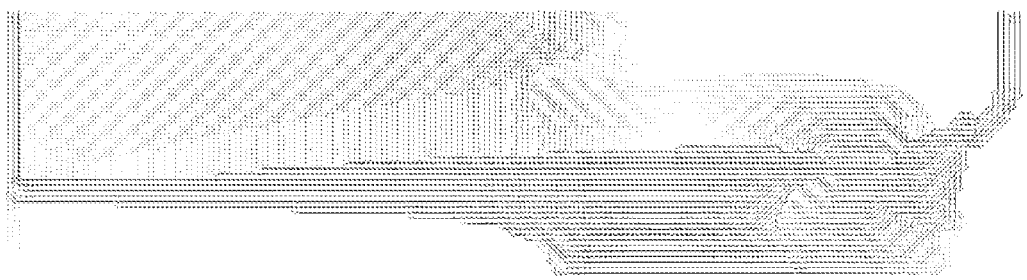
FIG. 4b illustrates exemplary results of the current flow in a tooth with secondary caries under an amalgam filling in relation to the directions of the current flow in accordance with an embodiment of the invention.

The employed models and the results are presented in FIGS. 3 and 4. FIGS. 3a and 4a demonstrate the distribution of tissues representing different electrical properties on a tooth cross section. Different shades of color mark enamel, dentine and pulp. The electrode placed on the tooth was also marked.

The amalgam filling in the vicinity of secondary caries area is shown in FIG. 4a. The simulated current direction flow is marked with fine lines in FIGS. 3b and 4b.

Figure 4C:
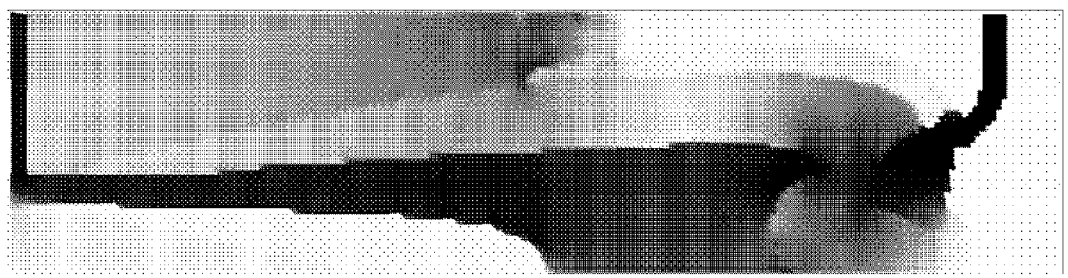
FIG. 4c illustrates exemplary results of the current flow in a tooth with a secondary caries under an amalgam filling in relation to the current density distribution in accordance with an embodiment of the invention.

A map of current density calculated in the simulation is presented in FIGS. 3c and 4c. White areas mark the lowest current densities while the black ones the highest current densities.

It can be read from the simulation results that the highest current densities are observed in the pulp and in the dentine in the area between the point the electrode is placed and the point of the pulp located nearest to it.

The current density increases in the tooth with filling because of good electrical conductivity of amalgam and the decrease of the thickness of dentine layer that has worse electrical conductivity.

It causes still higher concentration of the lines representing current flow in the area where secondary caries may occur making the harmonic response characteristic of the carious tissue easier to measure.

EXAMPLE 2

The device for secondary caries detection consists of a casing in which a current generating device 6 is located. The current generating device 6 contains high linearity amplifiers. The generated current has the form of sinusoidally varying signal of a frequency of 100 kHz.

A fixed electrode 2 is connected to the measuring current generating device 6 at one side and a movable electrode 1 the one placed on the tooth is connected at the other side.

A plurality of preamplifiers of high sensitivity and linearity a phase-sensitive detectors measuring components of a frequency of 100 kHz as well as its five multiples is connected to the above-mentioned electrode in parallel A microprocessor control unit 5 with a miniature keyboard and display unit is connected to the plurality of preamplifiers 4 at one side and to the measuring current generating device 6 at the other side.

The measuring current generating device 6 produces measuring current that flows through the movable electrode 1 placed on a tooth and the fixed electrode 2.

Figure 1:
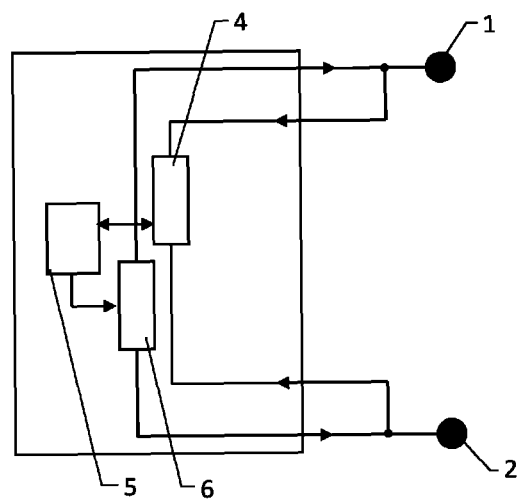
FIG. 1 illustrates a schematic view of a caries detection in accordance with a first embodiment of the invention.

Then the signal is read and amplified in the plurality of preamplifiers 4. The measuring current generating device 6 is controlled by the provided microprocessor control unit 5 which is connected to the plurality of preamplifiers 4. The schematic diagram of the device is demonstrated in FIG. 1.

EXAMPLE 3

Figure 2:
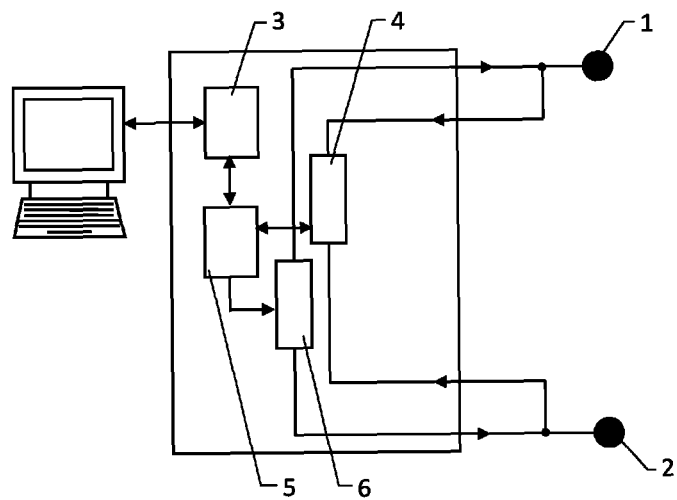
FIG. 2 is a schematic view of a caries detection device in accordance with a second embodiment of the invention.

The device as described in the example 2 containing an interface 3 to be connected to the peripheral device connected with the microprocessor control unit 5. A computer has been connected to the interface. The schematic diagram of the device is demonstrated in FIG. 2.

EXAMPLE 4

In vitro Results on Extracted Teeth

Figure 5:
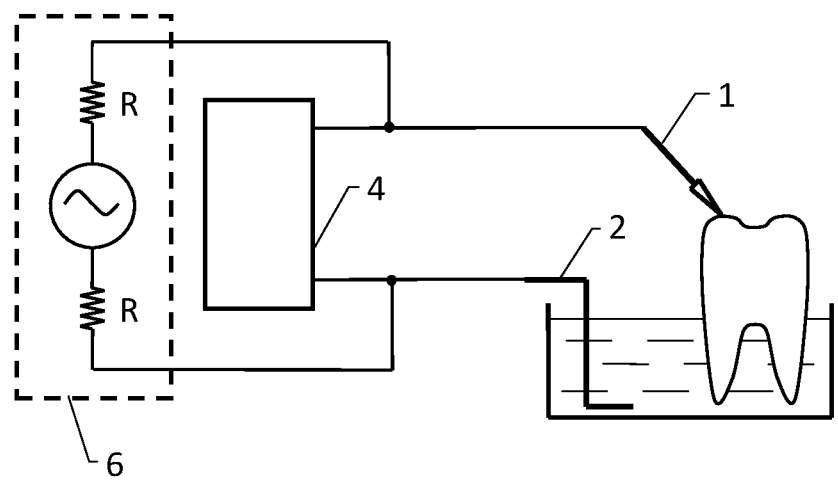
FIG. 5 illustrates schematic view of the setup used for in vitro measurements in accordance with an embodiment of the invention.

Measurements have been made on teeth extracted a few days earlier. The root of each tooth as well as the fixed electrode 2 were immersed in 0.9% aqueous solution of NaCl called saline solution. The tip of a standard dental explorer was used as the moveable electrode 1. Saline solution was also used to keep the teeth wet during measurements to simulate the conditions in the oral cavity. A sinusoidal signal of 1 kHz frequency and 2.5 V amplitude was applied to the electrodes 1 and 2 through 2×10 kΩ series resistors R and the response was analyzed in a digital harmonic analyzer 4, as depicted in FIG. 5.

Figure 6:
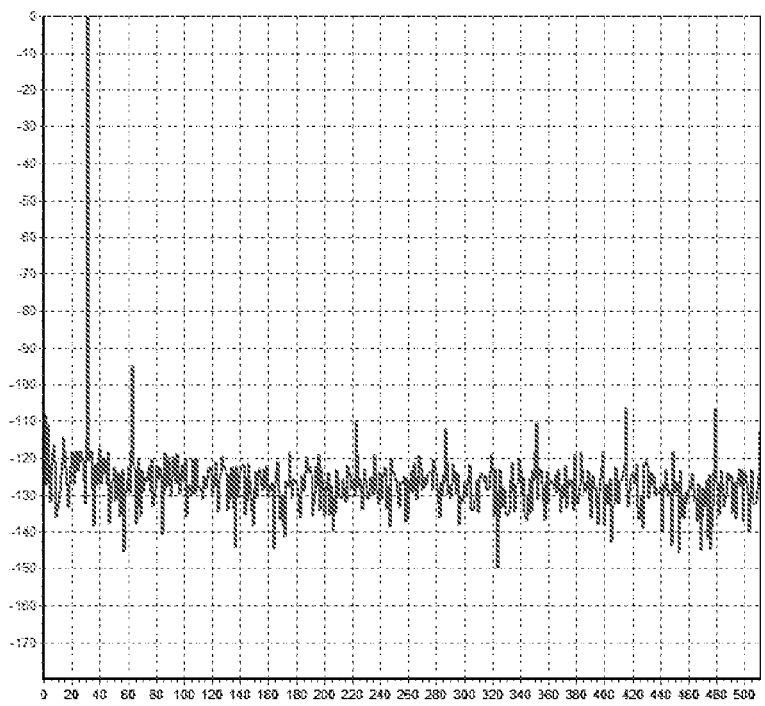
FIG. 6 shows exemplary results obtained for a sound extracted tooth in accordance with an embodiment of the invention.
Figure 7:
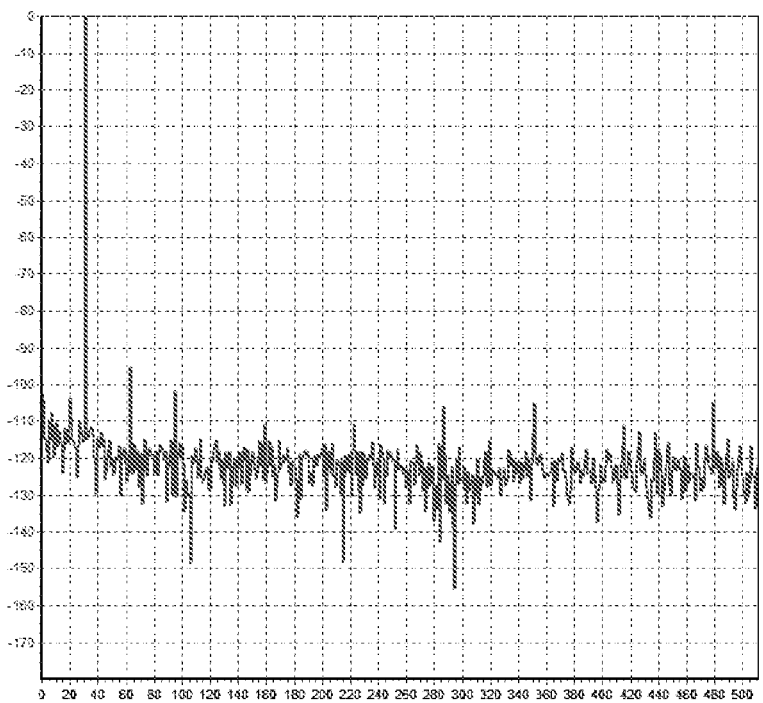
FIG. 7 shows exemplary results obtained for a sound tooth with filling in accordance with an embodiment of the invention.
Figure 8:
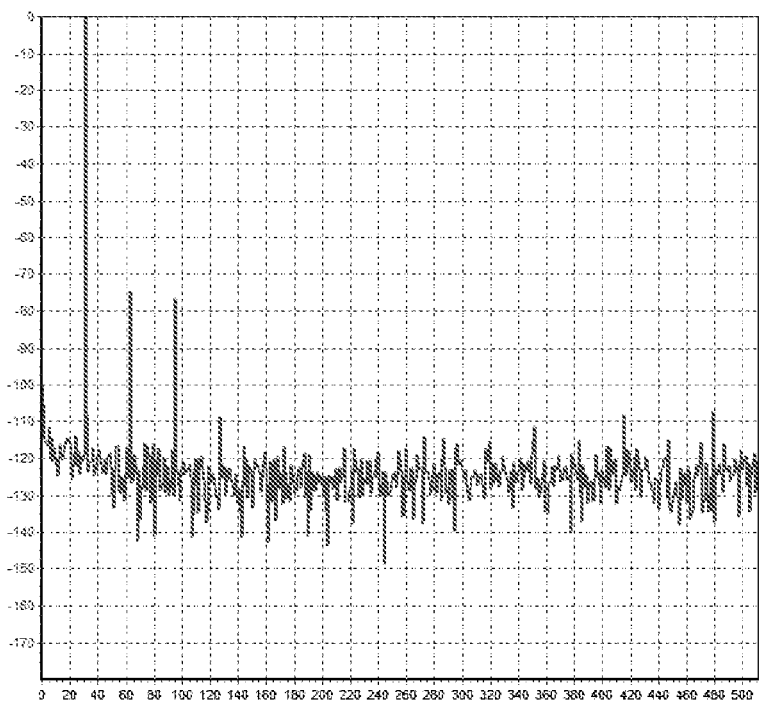
FIG. 8 shows the exemplary results obtained for a tooth with filling and addition of bacteria, namely *Lactobacillus acidophilus*, in accordance with an embodiment of the invention.

The measurements were conducted on sound teeth, in which a dentist made composite fillings, either clean or with addition of bacteria (namely *Lactobacillus acidophilus*). The screenshots in FIGS. 6 to 8 represent the results obtained with the harmonic analyzer. The results are presented in frequency domain, i.e., the horizontal axis is a frequency axis with $\frac{1}{32}$ kHz unit. The peaks at 32, 64, 96, etc. correspond to the excitation frequency 1 kHz and its harmonics, i.e., 2 kHz, 3 kHz, etc. The Y axis is the intensity of the tooth response at each frequency presented in logarithmic scale with respect to the excitation frequency response, i.e., the fundamental peak 1 kHz is always at 0 dB. The sensitivity threshold of the device used is about −100 dB for the second and third harmonic, and about −110 dB for higher harmonics; the peaks appearing below this level are artifacts.

Measurable harmonics were registered only when (living) bacteria were present (added) under the filling. In such cases, a non-linear bio-impedance spectrum of bacteria was obtained. FIG. 6 shows example results obtained for an extracted sound tooth (no filling and no bacteria added).

FIG. 7 shows example results for a sound tooth with clean (no bacteria added) filling made by a dentist. FIG. 8. shows example results obtained for a sound tooth where bacteria were added under the filling. These results were reproduced for different teeth.

The invention claimed is:

1. A secondary caries detection device comprising:
   a current generating device configured to generate a current having the form of a sinusoidally varying signal and having a chosen frequency from the range of frequencies from 200 Hz to 100 kHz and a chosen amplitude from the range of 50 mV to 5 V;
   a plurality of preamplifiers having phase sensitive measuring components sensitive to the chosen frequency and to integral multiples of the chosen frequency;
   a microprocessor control unit connected to the current generating device and the preamplifiers;
   at least one fixed electrode configured for placement on a mucous membrane of an oral cavity and connected to the current generating device and to the preamplifiers; and
   at least one movable electrode configured for placement on a surface of a tooth and connected to the current generating device and to the preamplifiers;
   wherein simultaneous with an application of the current having the chosen frequency from the current generating device to the electrodes, the microprocessor control unit is configured to measure an amplitude and phase of an electrical response at the electrodes at the chosen frequency and at integral multiples of the chosen frequency to provide a response spectrum.

2. The secondary caries detection device according to claim 1, wherein the microprocessor control unit further comprises an interface configured to cooperate with an external device.

3. The secondary caries detection device according to claim 1, wherein the current generating device comprises a plurality of high linearity amplifiers.

4. The secondary caries detection device according to claim 1, wherein the microprocessor control unit further comprises a miniature keyboard and a display unit.

5. The method of claim 1, wherein the integral multiples of the chosen frequency consist of frequencies up to 1 MHz.

6. The method of claim 1, wherein the chosen frequency is 100 kHz, and wherein the phase sensitive measuring components of the preamplifiers are sensitive to the chosen frequency of 100 kHz and to five integral multiples of 100 kHz.

7. A method for detection of secondary caries using at least one movable electrode placed on a surface of an examined tooth and at least one fixed electrode secured on a mucous membrane of an oral cavity in the vicinity of the examined tooth, comprising:
   a) supplying to the electrodes an electrical stimulation signal having the form of a sinusoidally varying current and having a chosen frequency from the range of frequencies from 200 Hz to 100 kHz and a chosen amplitude from the range of 50 mV to 5 V;
   b) simultaneous with supplying to the electrodes the electrical stimulation signal having the chosen frequency, measuring an amplitude and phase of an electrical response at the electrodes at the chosen frequency and integral multiples of the chosen frequency to provide a response spectrum; and
   c) analyzing the response spectrum to identify features characteristic of secondary caries.

8. The method according to claim 7, wherein the step of analyzing comprises:
   identifying features of the response spectrum that are correlated with a presence of bacteria that cause caries.

9. The method according to claim 7, wherein the movable electrode is placed on a surface of an amalgam filling.

* * * * *